(12) United States Patent
Arnin et al.

(10) Patent No.: US 8,262,661 B2
(45) Date of Patent: Sep. 11, 2012

(54) SPINAL REAMER

(75) Inventors: Uri Arnin, Kiryat Tivon (IL); Shai Fleischer, Haifa (IL)

(73) Assignee: Premia Spine Ltd., Ramat Poleg (IL)

( * ) Notice: Subject to any disclaimer, the term of this patent is extended or adjusted under 35 U.S.C. 154(b) by 720 days.

(21) Appl. No.: 11/692,196

(22) Filed: Mar. 28, 2007

(65) Prior Publication Data

US 2007/0270865 A1 Nov. 22, 2007

Related U.S. Application Data

(60) Provisional application No. 60/789,219, filed on Apr. 5, 2006.

(51) Int. Cl.
*A61B 17/00* (2006.01)
(52) U.S. Cl. ........................................................ 606/85
(58) Field of Classification Search .................... 606/80, 606/87, 96, 85; 83/565
See application file for complete search history.

(56) References Cited

U.S. PATENT DOCUMENTS

| | | | |
|---|---|---|---|
| 3,835,859 A | 9/1974 | Roberts et al. | |
| 3,865,162 A * | 2/1975 | Schmidt | 144/144.1 |
| 4,319,615 A * | 3/1982 | Ditmanson | 144/144.1 |
| 5,038,646 A * | 8/1991 | Suwitoadji | 83/56 |
| 5,344,423 A * | 9/1994 | Dietz et al. | 606/87 |
| 5,918,524 A * | 7/1999 | Kirby | 83/565 |
| 6,332,887 B1 * | 12/2001 | Knox | 606/87 |
| 7,083,625 B2 * | 8/2006 | Berry | 606/96 |
| 7,189,240 B1 * | 3/2007 | Dekel | 606/85 |
| 2002/0058944 A1 * | 5/2002 | Michelson | 606/79 |
| 2004/0002711 A1 * | 1/2004 | Berry | 606/79 |
| 2005/0273110 A1 | 12/2005 | Boehm | |
| 2006/0030854 A1 | 2/2006 | Haines | |
| 2006/0089609 A1 * | 4/2006 | Bleich et al. | 604/272 |

FOREIGN PATENT DOCUMENTS

| | | |
|---|---|---|
| GB | 1571926 | 7/1980 |
| WO | 01/08571 | 2/2001 |

OTHER PUBLICATIONS

Written Opinion, PCT Application PCT/IL2007/000402.

* cited by examiner

*Primary Examiner* — Kevin T Truong
*Assistant Examiner* — David Bates
(74) *Attorney, Agent, or Firm* — Dekel Patent Ltd; David Klein

(57) ABSTRACT

Spinal reamer apparatus including a reference base with mounting provisions for mounting in a region of posterior lumbar spinal structure, a non-straight track fixed to the reference base, and at least one reaming cutter element arranged to move along the track.

9 Claims, 9 Drawing Sheets

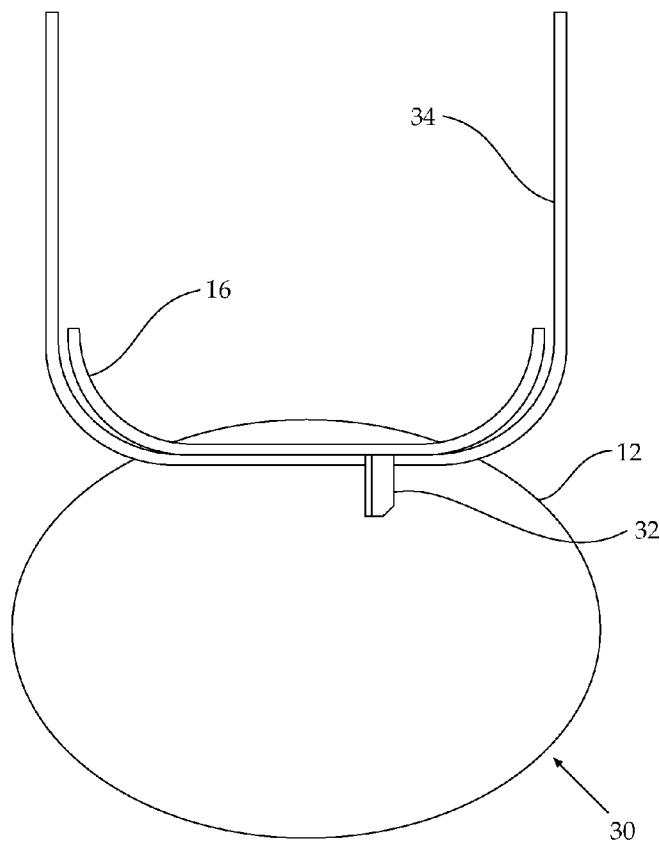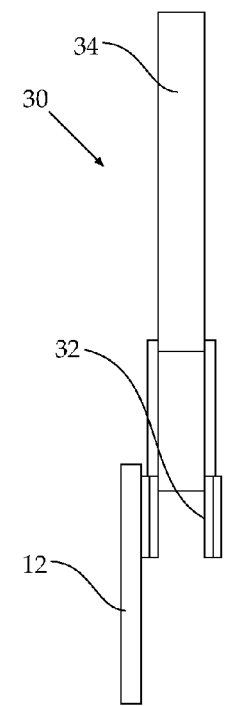
FIG. 4A
FIG. 4C
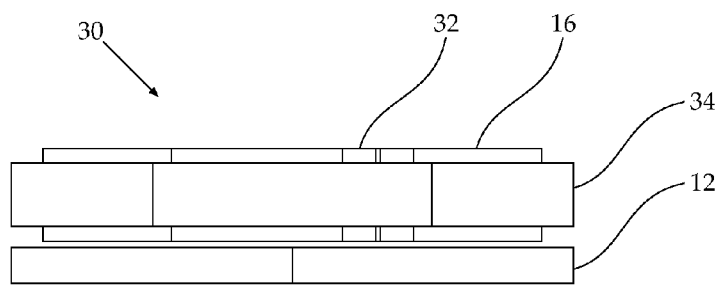
FIG. 4B

SPINAL REAMER

CROSS-REFERENCE TO RELATED APPLICATIONS

This application claims priority under 35 USC §119 to U.S. Provisional Patent Application Ser. No. 60/789,219, filed on Apr. 5, 2006, which is incorporated herein by reference.

FIELD OF THE INVENTION

The present invention relates to spinal reamers for use in surgical procedures, such as installing spinal prostheses.

BACKGROUND OF THE INVENTION

Spinal disc or partial spinal disc replacement is a common procedure in Europe with thousands having been performed already and is now commencing in the United States. Examples of such replacement discs are ProDisc (Spine Solutions, Inc.) and SB Charite III (Link Spine Group, Inc.)

By replacing a disc and not merely fusing vertebrae, which is the common alternative practice to disc replacement, the mobility of the patient's adjacent discs may be preserved and thus may delay the onset of arthritic changes to adjacent vertebrae.

A typical disc replacement unit is approximately 30 millimeters in diameter. This relatively large cross-section usually necessitates a mostly anterior retroperitoneal (from the front of the abdomen but staying outside the intestinal sac) approach to the spine which may be risky. The risks of general anesthesia are coupled with risks of vascular injury and retrograde ejaculation in males.

Although many prosthetic disc devices are described in the literature, there is still a need for improvement in ease of manufacture and performance and of the preparation of the space for the insertion of the prosthesis.

SUMMARY OF THE INVENTION

The present invention seeks to provide spinal reamers for use in surgical procedures, such as installing spinal prostheses, as is described more in detail hereinbelow. For example, following transforaminal posterior lumbar discectomy, a portion of the disc and endplate may remain behind. The spinal reamer apparatus may be used to ream, cut and/or remove material or debris.

BRIEF DESCRIPTION OF THE DRAWINGS

In the drawings:

FIGS. 4A, 4B and 4C are simplified top-view, front-view and side-view illustrations, respectively, of spinal reamer apparatus, constructed and operative in accordance with another embodiment of the present invention, including a single reaming cutter element on a band saw blade;

DESCRIPTION OF EMBODIMENTS

Figure 1A:
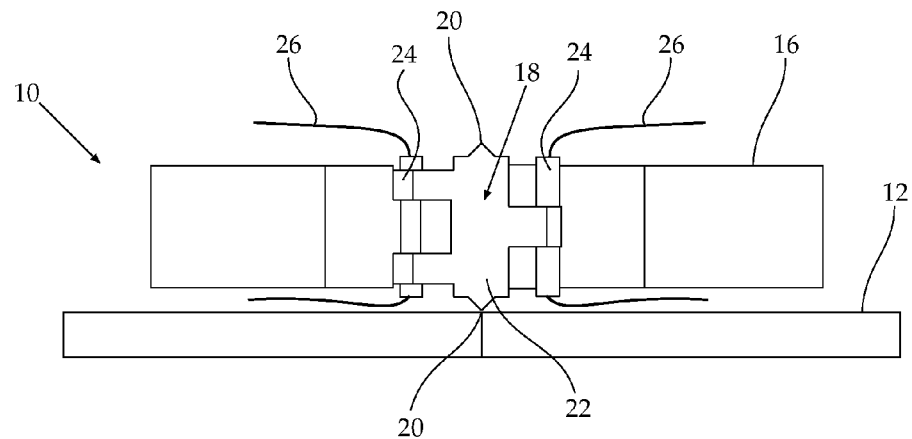
FIGS. 1A and 1B are simplified top-view and front-view illustrations, respectively, of spinal reamer apparatus, constructed and operative in accordance with an embodiment of the present invention, including a single reaming cutter element arranged to move along a track.
Figure 1B:
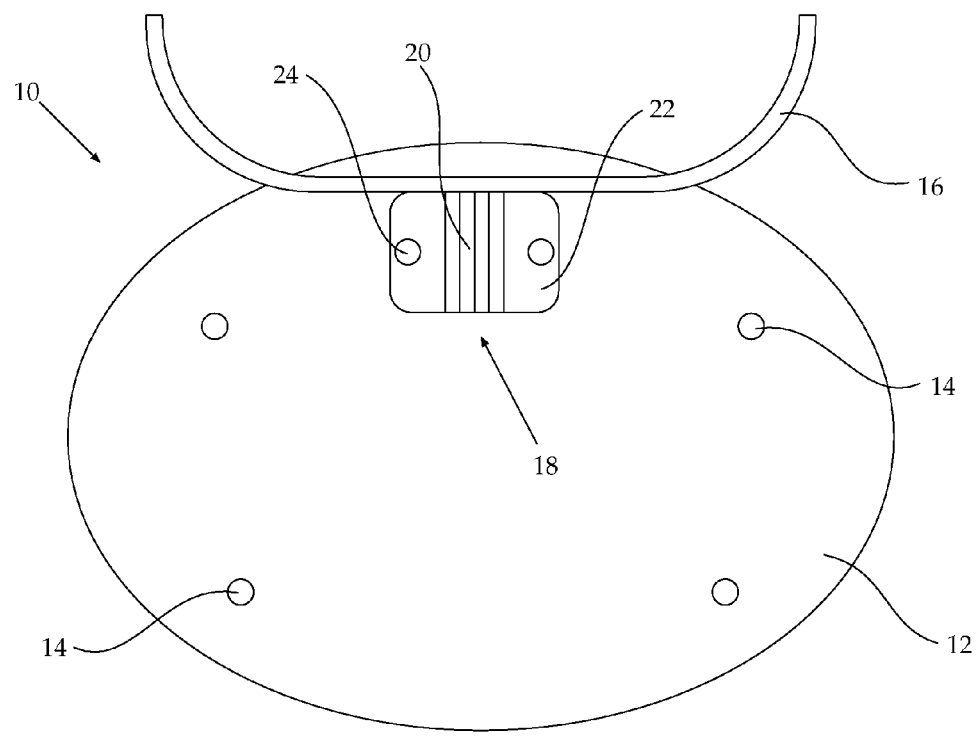

Reference is now made to FIGS. 1A and 1B, which illustrate spinal reamer apparatus 10, constructed and operative in accordance with a non-limiting embodiment of the present invention.

Spinal reamer apparatus 10 includes a reference base 12 with mounting provisions 14 for mounting in a region of posterior lumbar spinal structure. For example, mounting provisions 14 may be mounting holes positioned to correspond with the exact position of mounting hardware (e.g., pedicle screws) or mounting holes of a spinal prosthesis (not shown) to be installed in the spine, e.g., posterior spinal structure or intravertebral or intervertebral space. For example, mounting provisions 14 may be mounting holes positioned to correspond with the exact position of holes drilled into bone for mounting pedicle screws of the implant described in U.S. Pat. No. 7,011,685, the disclosure of which is incorporated herein by reference.

A track 16 may be fixed to reference base 12. Track 16 in the non-limiting illustrated embodiment is non-straight, such as being arcuate. Track 16 may also shield spinal tissue from the reaming element.

A reaming cutter element 18 is arranged to move along track 16. The reaming cutter element 18 may be rigid or flexible. The reaming cutter element 18 may be fashioned from any combination of materials used for cutting spinal bone and tissues, such as but not limited to, ceramic, aluminum oxide, zirconium oxide, metal, metal alloy, cobalt-chromium-tungsten-nickel alloy, cobalt-chromium-manganese alloy, cobalt-chromium alloy, cobalt-chromium-molybdenum alloy, chromium-nickel-manganese alloy, powder metal alloy, 316 L stainless steel, tool steel and many more. Reaming cutter element 18 may be used to ream, cut and/or remove disc material (e.g., annulus fibrosus, nucleus pulposus, cartilage and the like).

In the non-limiting illustrated embodiment, reaming cutter element 18 includes upper and lower cutting edges 20 at opposite ends of a cutter body 22. The cutter body 22 may include peripheral apertures 24, in which a cord 26 or other similar elongate member may be disposed for pulling (or pushing, depending on the stiffness of the cord 26) reaming cutter element 18 along track 16.

Figure 2A:
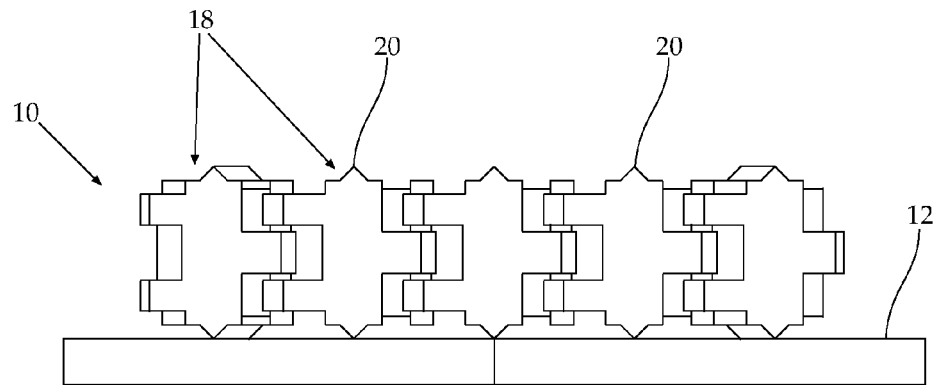
FIGS. 2A and 2B are simplified top-view and front-view illustrations, respectively, of spinal reamer apparatus, constructed and operative in accordance with another embodiment of the present invention, including a plurality of reaming cutter elements arranged to move along the track.
Figure 2B:
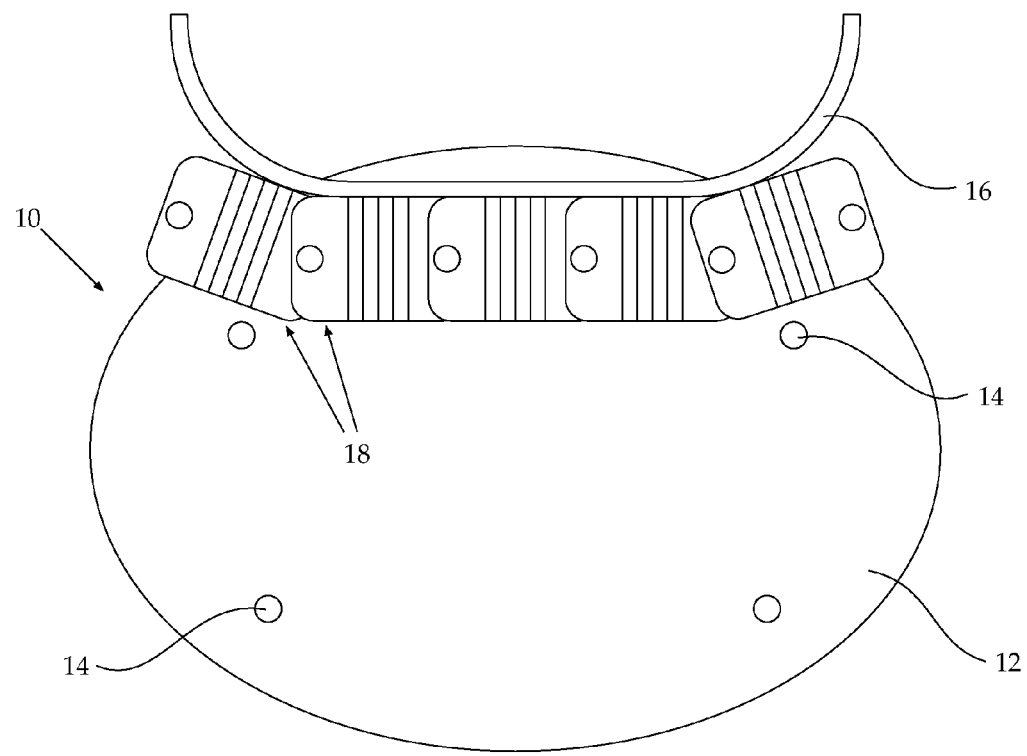

Reference is now made to FIGS. 2A and 2B, which illustrate spinal reamer apparatus 10, constructed and operative in accordance with another embodiment of the present invention. In this version, spinal reamer apparatus 10 includes a plurality of reaming cutter elements 18 arranged to move along track 16. The plurality of reaming cutter elements 18 may act similar to a chain-saw.

Figure 3:
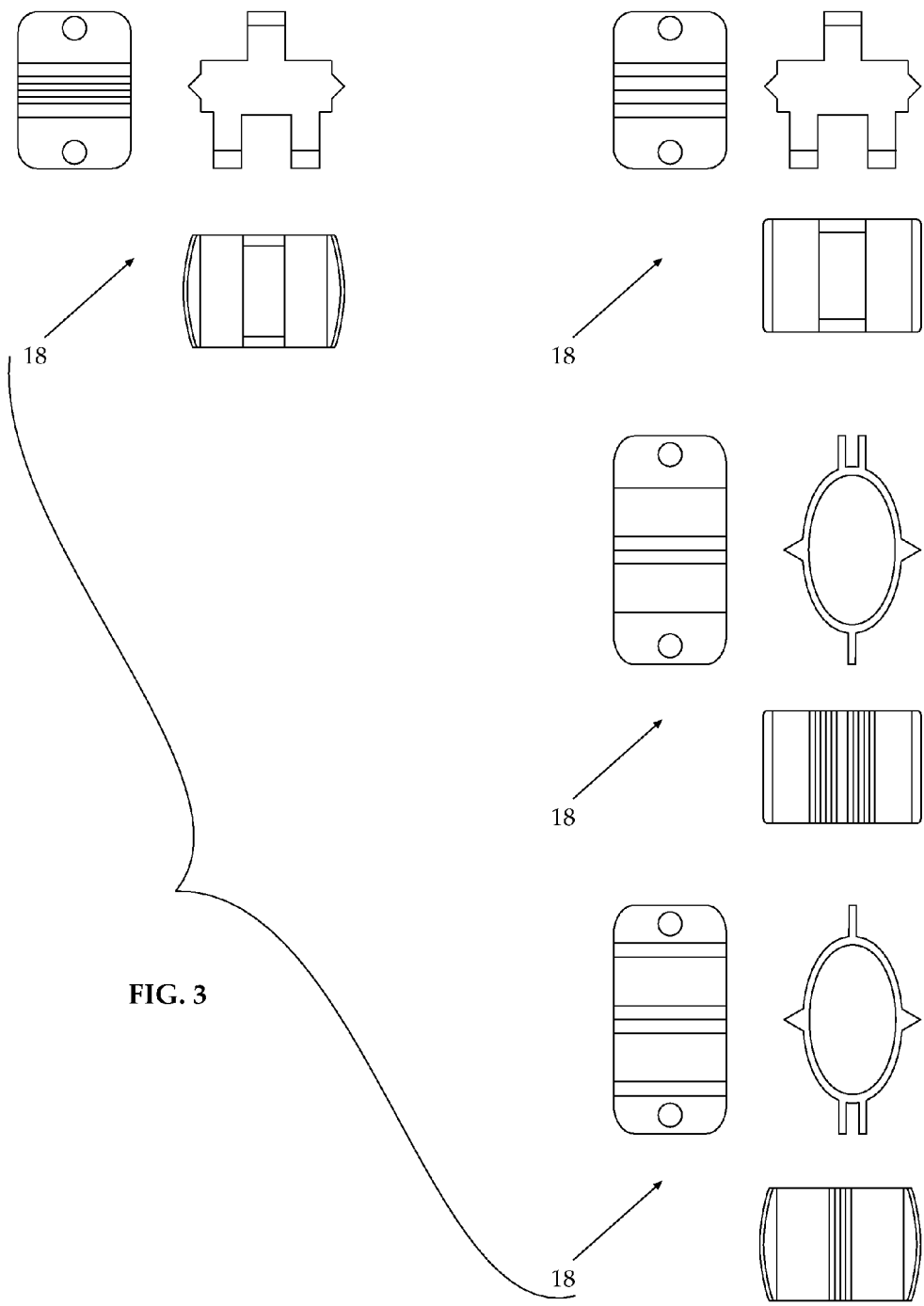
FIG. 3 is a simplified illustration of a set of reaming cutter elements useful in the spinal reamer apparatus of the invention.

Reference is now made to FIG. 3, which illustrates a set of reaming cutter elements 18 useful in the spinal reamer apparatus of the invention. It is noted that the reaming cutter elements are not necessarily identical, and may be provided in all sorts of sizes, shapes, cutting edges (e.g., straight, rounded, pointed, elongate, elliptic and many others), hardness, flexibility and other qualities and material properties.

Reference is now made to FIGS. 4A, 4B and 4C, which illustrate spinal reamer apparatus 30, constructed and operative in accordance with another embodiment of the present invention. This embodiment is basically the same as that of FIGS. 1A-1B, with like elements being designated by like reference numerals, except that spinal reamer apparatus 30 includes a reaming cutter element 32 on a band saw blade 34. The band saw blade 34 may be manipulated back and forth to move reaming cutter element 32 along track 16 and cut tissue. Reaming cutter element 32 may be constructed similarly to reaming cutter element 18.

Figure 5A:
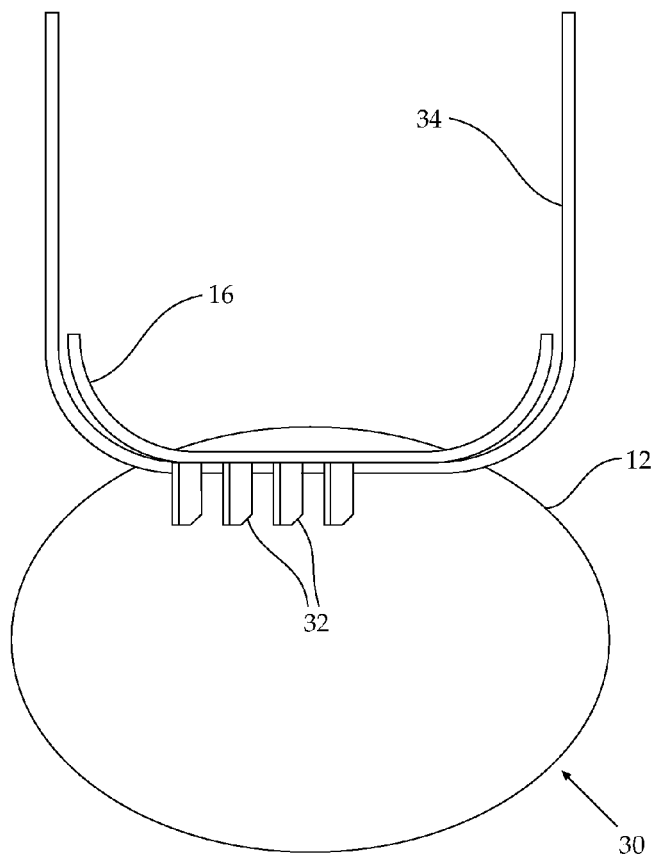
FIGS. 5A, 5B and 5C are simplified top-view, front-view and side-view illustrations, respectively, of spinal reamer apparatus, constructed and operative in accordance with another embodiment of the present invention, including a plurality of reaming cutter elements on the band saw blade.
Figure 5C:
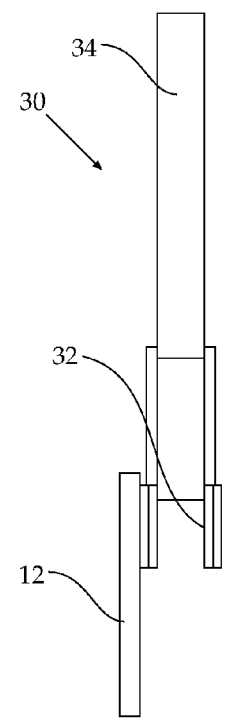
Figure 5B:
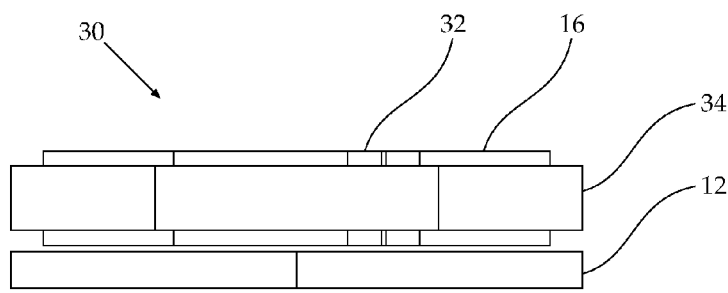

Reference is now made to FIGS. 5A, 5B and 5C, which illustrate spinal reamer apparatus 30, constructed and operative in accordance with another embodiment of the present invention. In this version, spinal reamer apparatus 30 includes a plurality of reaming cutter elements 32 on band saw blade 34.

Figure 6A:
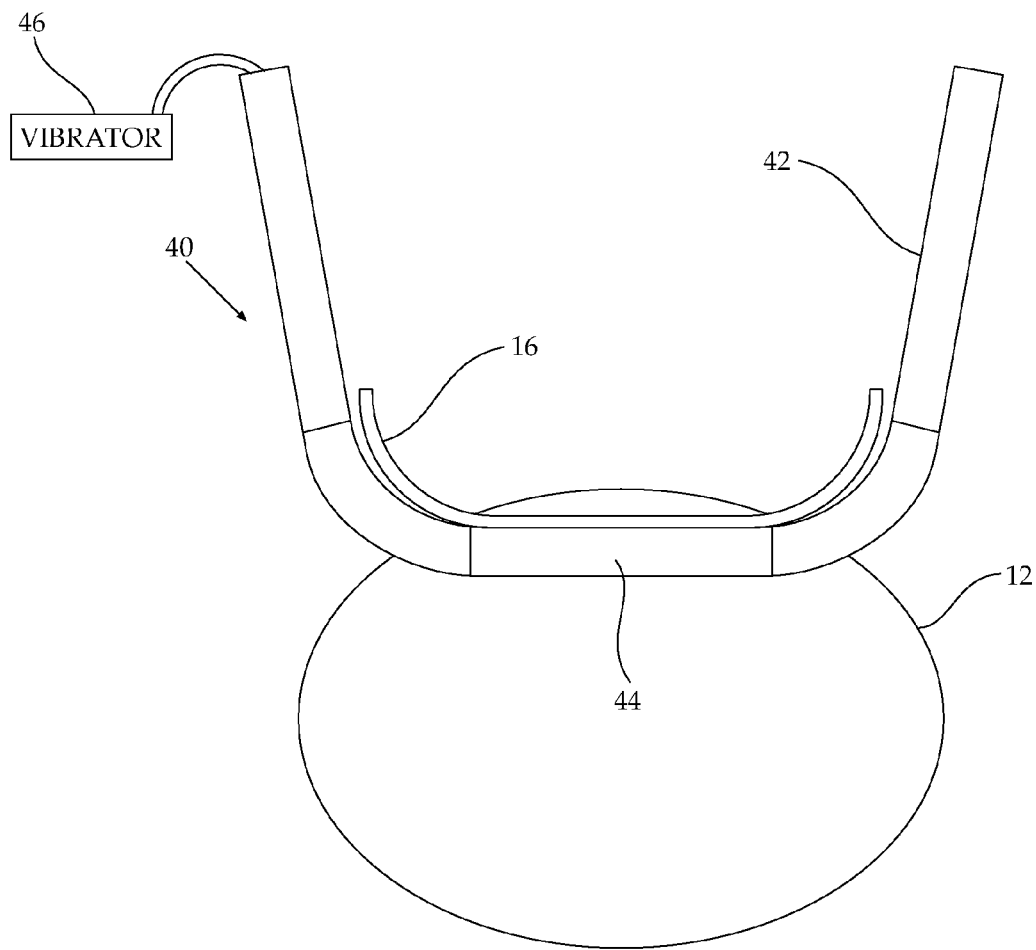
FIGS. 6A and 6B are simplified top-view and front-view illustrations, respectively, of spinal reamer apparatus, constructed and operative in accordance with another embodiment of the present invention, including a reaming cutter element with abrasive surfaces.
Figure 6B:
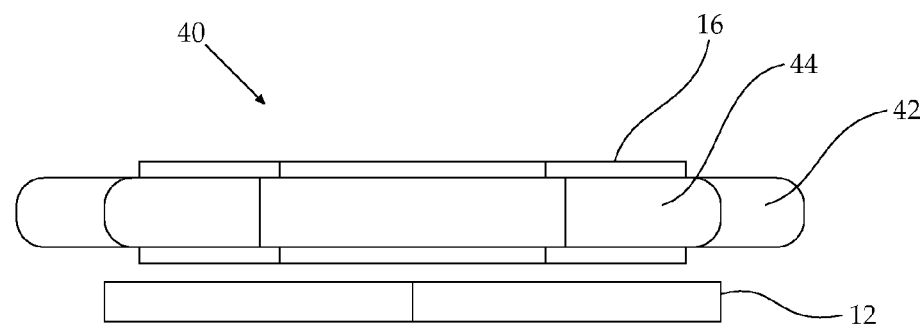

Reference is now made to FIGS. 6A and 6B, which illustrate spinal reamer apparatus 40, constructed and operative in accordance with another embodiment of the present invention. In this embodiment, spinal reamer apparatus 40 includes a reaming cutter element 42 with abrasive surfaces 44. For example, the abrasive surfaces 44 may be carborundum or other abrasive material coated or otherwise deposited on reaming cutter element 42. In accordance with a non-limiting embodiment of the invention, a vibrator 46 may be coupled to reaming cutter element 42. The vibrator 46 may be, without limitation, a motor that rotates an eccentric weight on a shaft or an oscillating weight, or an ultrasonic or piezoelectric vibrating device. Vibrator 46 sets up vibrations in reaming cutter element 42 and may improve or accelerate cutting of tissue. Vibrator 46 may be used with any of the embodiments of the invention.

Figure 7A:
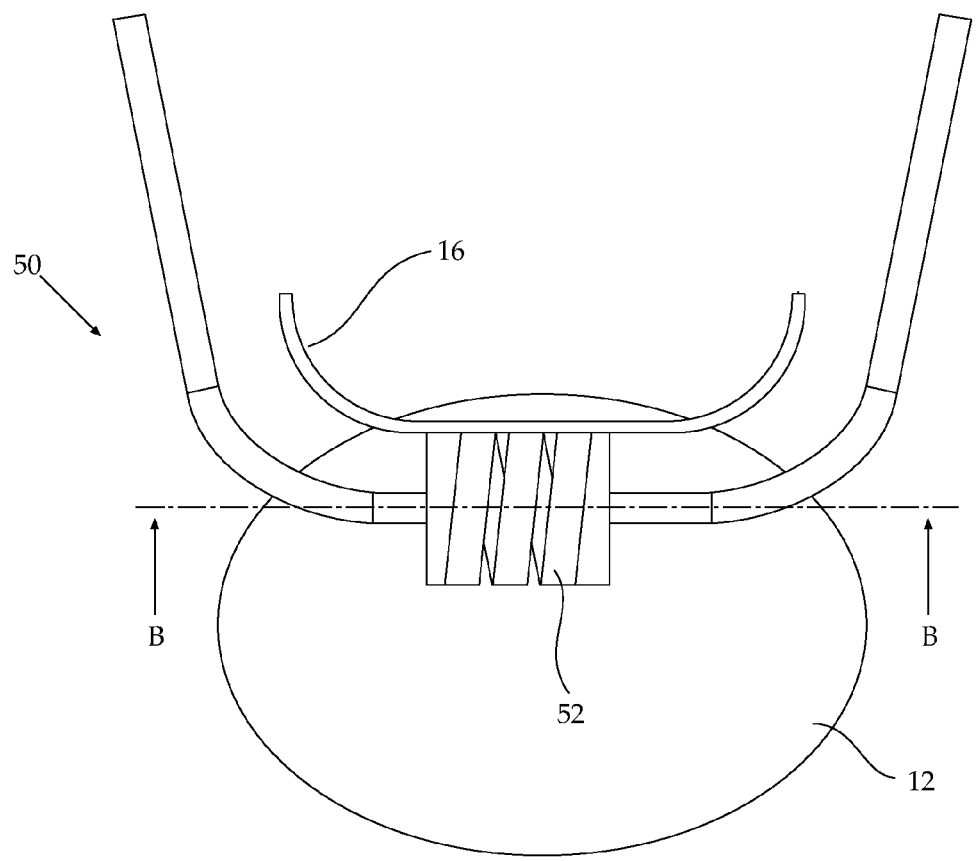
FIGS. 7A and 7B are simplified top-view and front-sectional-view illustrations, respectively, of spinal reamer apparatus, constructed and operative in accordance with another embodiment of the present invention, including a spiral reaming cutter element.
Figure 7B:
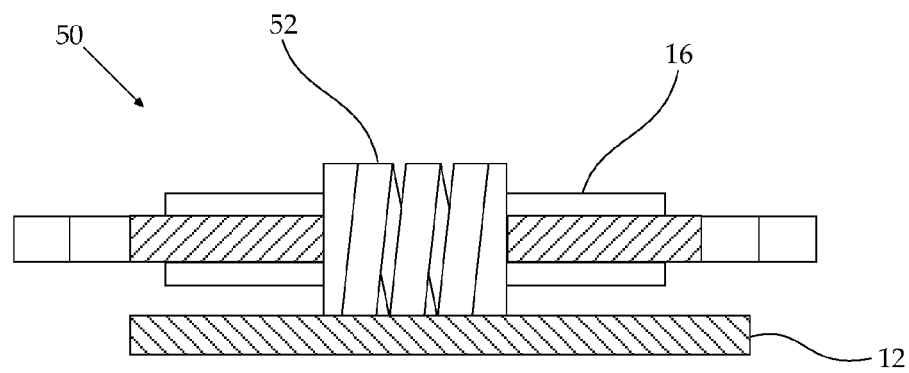

Reference is now made to FIGS. 7A and 7B, which illustrate spinal reamer apparatus 50, constructed and operative in accordance with another embodiment of the present invention. In this embodiment, spinal reamer apparatus 50 includes a spiral reaming cutter element 52, with cutting edges all along (or partially along) the spirals. Disc material may flow into the internal space of spiral reaming cutter element 52 during reaming.

Figure 8A:
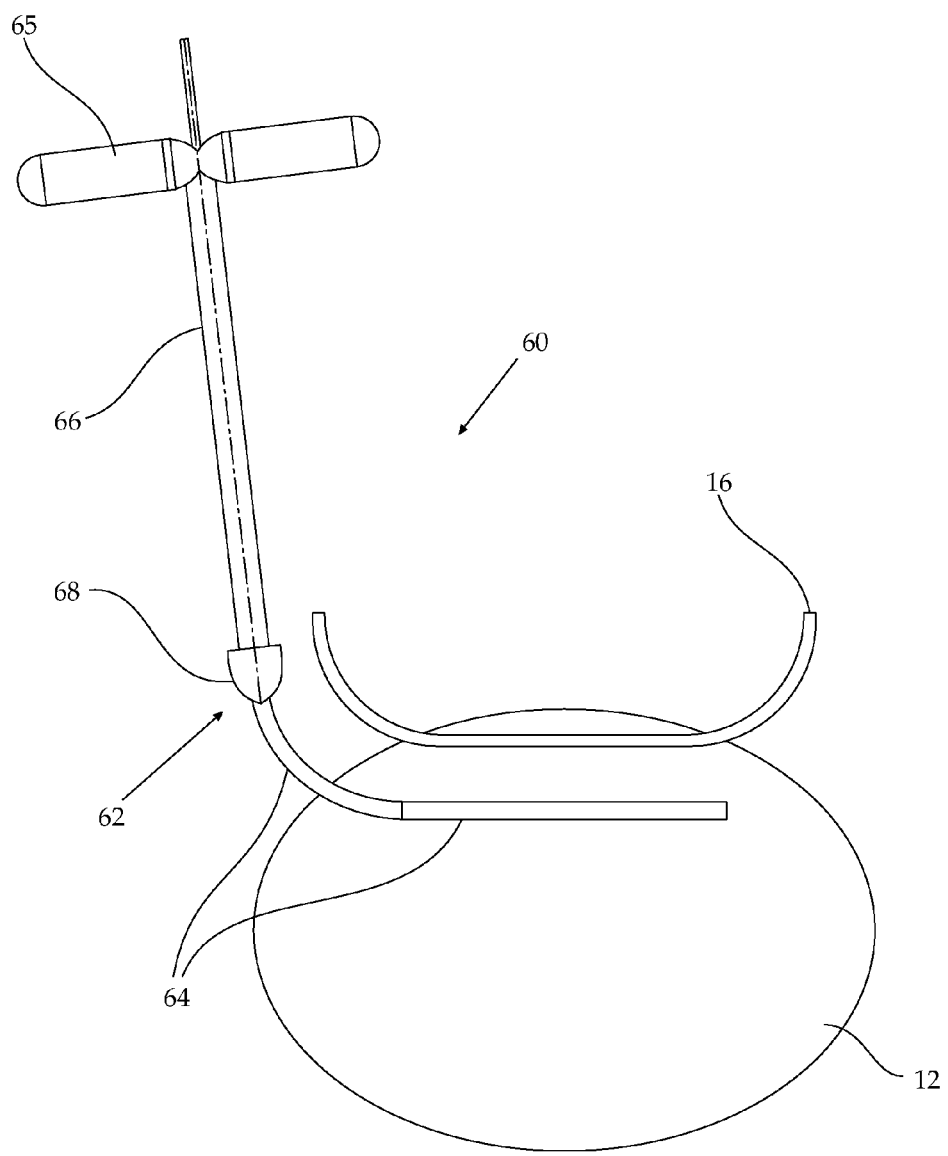
FIGS. 8A and 8B are simplified top-view and front-view illustrations, respectively, of spinal reamer apparatus, constructed and operative in accordance with another embodiment of the present invention, including a rotating reaming cutter element.
Figure 8B:
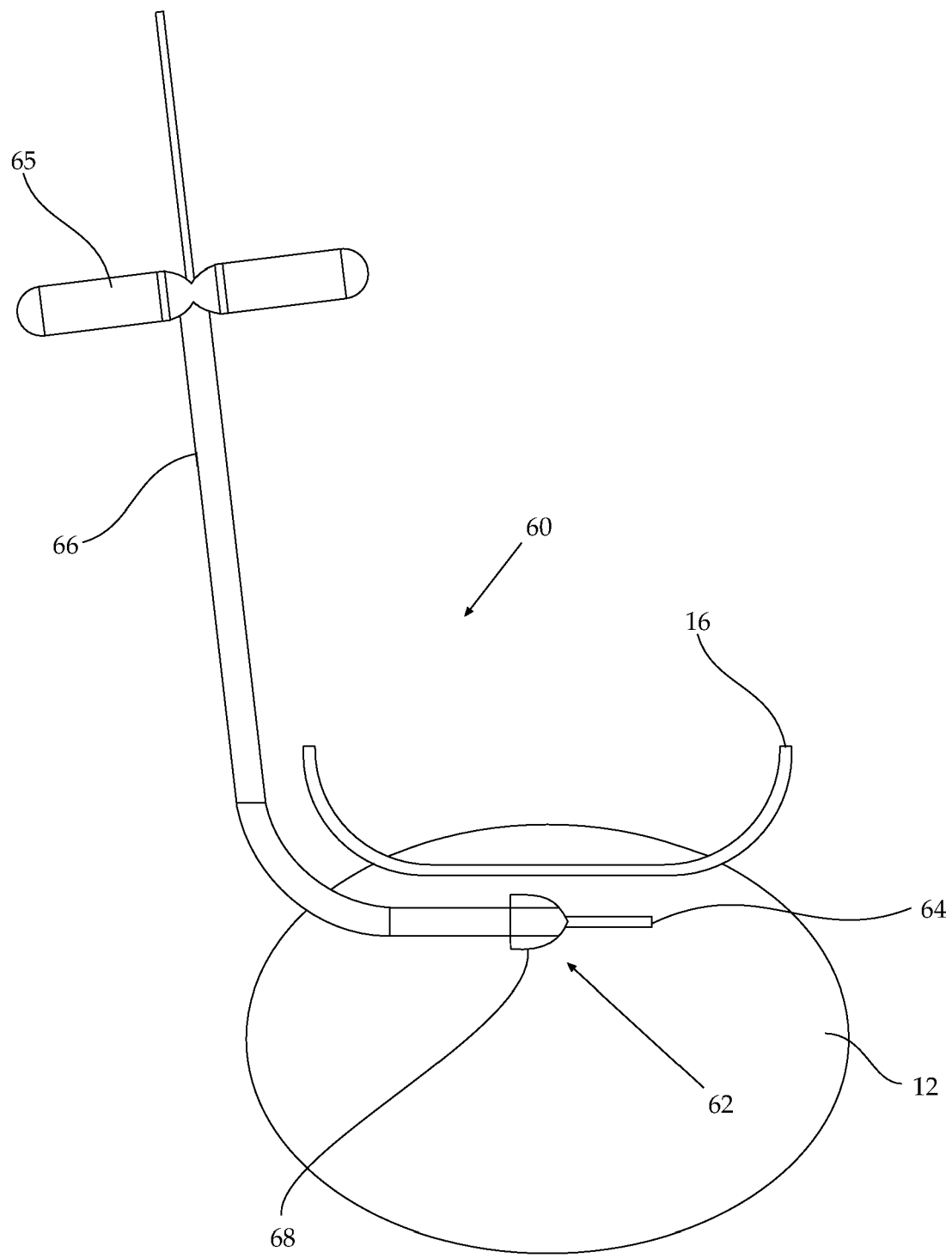

Reference is now made to FIGS. 8A and 8B, which illustrate spinal reamer apparatus 60, constructed and operative in accordance with another embodiment of the present invention. In this embodiment, spinal reamer apparatus 60 includes a rotating reaming cutter element 62. A rigid guide 64 may be inserted into the spinal space. A flexible shaft 66 may be connected to a reamer head 68, and inserted into the rigid guide 64. The flexible shaft 66 and the reamer head 68 may be rotated manually or electrically, such as by means of an operating handle 65, and advanced along guide 64. Reamer head 68 can be fashioned in any shape or size for different types of cleaning, removing or reaming.

Although the invention has been described in conjunction with specific embodiments thereof, it is evident that many alternatives, modifications and variations will be apparent to those skilled in the art. Accordingly, it is intended to embrace all such alternatives, modifications and variations.

What is claimed is:

1. Spinal reamer apparatus comprising:
   a planar, flat reference base with mounting provisions for mounting in a region of posterior lumbar spinal structure, wherein said mounting provisions are mounting holes formed through a thickness of said reference base, the thickness being less than a width or length of said reference base;
   a non-straight track immovable with respect to said reference base, wherein the track and reference base do not intersect each other and the track is substantially parallel to the reference base; and
   at least one reaming cutter element arranged to move along said track, wherein said at least one reaming cutter element is flexible.

2. The spinal reamer apparatus according to claim 1, further comprising a plurality of reaming cutter elements arranged to move along said track, wherein at least one of the reaming cutter elements is not identical to another of the reaming cutter elements.

3. The spinal reamer apparatus according to claim 1, wherein said at least one reaming cutter element comprises upper and lower cutting edges at opposite ends of a cutter body.

4. The spinal reamer apparatus according to claim 1, wherein said at least one reaming cutter element is mounted on a band saw blade.

5. The spinal reamer apparatus according to claim 1, wherein said at least one reaming cutter element comprises abrasive cutting surfaces.

6. The spinal reamer apparatus according to claim 1, wherein said at least one reaming cutter element comprises a spiral cutting element.

7. The spinal reamer apparatus according to claim 1, wherein said at least one reaming cutter element comprises a rotatable cutting element.

8. The spinal reamer apparatus according to claim 1, further comprising a vibrator coupled to said at least one reaming cutter element.

9. The spinal reamer apparatus according to claim 1, further comprising an elongate member attached to said at least one reaming cutter element for moving said at least one reaming cutter element along said track.

* * * * *